United States Patent
Knopff et al.

(10) Patent No.: US 9,879,203 B2
(45) Date of Patent: Jan. 30, 2018

(54) INTERMEDIATES AND PROCESS FOR THE PREPARATION OF SANDALWOOD OIL BUILDING BLOCKS

(71) Applicant: Firmenich SA, Geneva (CH)

(72) Inventors: Oliver Knopff, Geneva (CH); Fabien Fonteny, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 15/529,300

(22) PCT Filed: Nov. 16, 2015

(86) PCT No.: PCT/EP2015/076702
§ 371 (c)(1),
(2) Date: May 24, 2017

(87) PCT Pub. No.: WO2016/087179
PCT Pub. Date: Jun. 9, 2010

(65) Prior Publication Data
US 2017/0260477 A1    Sep. 14, 2017

(30) Foreign Application Priority Data
Dec. 2, 2014    (EP) .................................... 14195835

(51) Int. Cl.
*C11B 9/00*    (2006.01)

(52) U.S. Cl.
CPC .......... *C11B 9/0046* (2013.01); *C11B 9/0042* (2013.01)

(58) Field of Classification Search
CPC ................................................... C11B 9/0046
See application file for complete search history.

(56) References Cited

U.S. PATENT DOCUMENTS 4,223,167 A * 9/1980 Willis ....................... C07C 1/24
549/265
4,510,319 A * 4/1985 Willis ..................... C07C 17/10
512/18

FOREIGN PATENT DOCUMENTS

| EP | 0 010 213 A2 | 4/1980 |
| WO | WO 2008/120175 A1 | 10/2008 |
| WO | WO 2010/067309 A1 | 6/2010 |
| WO | WO 2011/000026 A1 | 1/2011 |
| WO | WO 2013/064411 A1 | 5/2013 |

OTHER PUBLICATIONS

International Search Report and Written Opinion, application PCT/EP2015/076702 dated Feb. 11, 2016.
Arai et al., Bull. Chem. Soc. Jpn., 1988, vol. 61, pp. 467-473.
Bradfield et al., "65. α- and β- santalols", J. Chem. Soc., 1935, pp. 309-315.
Christenson et al., "East Indian Sandalwood Oil. 1.", J. Org. Chem., 1979, vol. 44, no 12, pp. 2012-2018.
Christenson et al., "East Indian Sandalwood Oil. 2.", J. Org. Chem., 1980, vol. 45, no 15, pp. 3068-3072.
Schalk et al., "Toward a Biosynthetic Route to Sclareol and Amber Odorants", J. Am. Chem. Soc., 2012, vol. 134, pp. 18900-18903.
Semmeler et al., in Chem. Ber., 1907, 40, pp. 3321-3324 (German language; see specification p. 2).
Takahashi and Shibasaki, "A New Method for the Introduction of Carbon-Carbon Triple Bond at C-13 in PG Synthesis", J. Org. Chem., 1988, vol. 53, pp. 1227-1231.
Simmons et al., "110. Aldehyde Enol Esters as Novel Chain Terminators in Cationic Olefin Cyclizations", Helv. Chim. Acta, 1988, vol. 71, pp. 1000-1004.
Snowden et al., "3. Stereoselective Syntheses of (±)-epi-β-Santalene and (±)-epi-β-Santalol", Helv. Chim. Acta, 1981, vol. 64, no 1, pp. 25-32.

* cited by examiner

*Primary Examiner* — Lanee Reuther
(74) *Attorney, Agent, or Firm* — Winston & Strawn LLP

(57) ABSTRACT

The present invention concerns a process for the preparation of an oxidized terpenes fraction which proved to be particularly useful in the preparation of sandalwood oil building blocks.

11 Claims, No Drawings

INTERMEDIATES AND PROCESS FOR THE PREPARATION OF SANDALWOOD OIL BUILDING BLOCKS

RELATED APPLICATIONS

This application is a national stage application under §371 of International Patent Application PCT/EP2015/076702, filed Nov. 16, 2015, which claims the benefit of European patent application no 14195835.5 filed Dec. 2, 2014.

TECHNICAL FIELD

The present invention relates to the field of organic synthesis and more specifically it concerns a process for the preparation of an oxidized terpenes fraction which proved to be particularly useful in the preparation of sandalwood oil building blocks.

PRIOR ART

The oxidized terpenes fraction (I) are novel composition of matter, and are useful starting materials for the preparation of sandalwood oil building blocks, in a short and effective manner.

The sandalwood oil is a well-known perfuming ingredient, of natural occurrence comprising a number of sesquiterpene allylic alcohols. However, because natural it is subject to variation in quantity and quality of the production, and therefore there is a need for alternative production of synthetic or natural oil as well as of building blocks to prepare or reconstitute it.

Recently, biotechnological methods to produce the related sesquiterpene hydrocarbon oil (i.e. oil as defined for the sesquiterpene hydrocarbons fraction (II) herein below) using host cells/microorganisms expressing recombinant santalene synthases have been reported. (e.g. WO 2011/000026 or WO 2010/067309). However, these methods do not allow to, nor suggest how to, convert said sesquiterpene hydrocarbon oil into analogues of sandalwood oil, or sandalwood oil building block (i.e. maintaining appropriate ratio of each constituent as close as possible to the natural oil, while converting an alkene into an allylic alcohol).

Indeed, the terpene synthases allow preparing fractions containing several sesquiterpene hydrocarbons (i.e. mixture of various different sesquiterpene hydrocarbons) and not a pure sesquiterpene hydrocarbon. Now, each constituent of such fractions of sesquiterpene hydrocarbons does have significantly different chemical structure, with different speed of reaction, possible chemoselectivity of reactive groups which render the chemistry needed to produce analogues of sandalwood oil, or sandalwood oil building block, extremely challenging.

To the best of our knowledge, the prior art reports a number of methods to chemically convert a relevant sesquiterpene hydrocarbon into a useful intermediate (i.e. an aldehyde as described in the invention oxidized terpenes fraction (I)), but this chemistry has been always performed on a pure sesquiterpene hydrocarbon. For instance one may cite:

Semmeler et al, in Chem. Ber., 1907, 40, 3321: this paper reports the ozonolysis of α-santalene, and of β-santalene separately, but the yield (not reported) must have been quite low considering that they report high difficulties in recovering "an aldehyde";

Bradfield et al, in J.C.S., 1935, 309: this paper reports the ozonolysis of pure α-santalene and β-santalene, and suggests that β-santalene produces considerable amount of CH2O suggesting that the exo-methylene group of β-santalene has also been attached;

Snowden et al, in Helv. Chim. Acta, 1981, 64, 25: where epi-β-santalene is oxidized into (I-A) using OsO4, NaIO4.

None of these methods suggests an industrial way to convert a sesquiterpene hydrocarbons fraction into a relevant sandalwood oil building block or intermediate thereof, as oxidized terpenes fraction (I). In fact, the teaching of these prior arts would even discourage to work on mixture of various different sesquiterpene hydrocarbons.

To the best of our knowledge, the prior art reports only a method to convert a mixture of sesquiterpene hydrocarbon into the corresponding sandalwood oil analogue (U.S. Pat. No. 4,510,319). However, this method used mixtures devoid of bergamotenes, which is a very sensitive substrate, used reagents such as $Ca(ClO)_2$, which is by far not the most suitable reagent industrially since halogenated intermediates can be produced.

The aim of the present invention is to provide a more industrial process for the preparation of sandalwood oil building block starting from the relevant mixture of terpenes.

DESCRIPTION OF THE INVENTION

A first object of the present invention is a composition of matter consisting in an oxidized terpenes fraction (I) comprising:

from 15 to 40% w/w of 3-((1S,2R,4R)-2-methyl-3-methylenebicyclo[2.2.1]heptan-2-yl)propanal, of formula

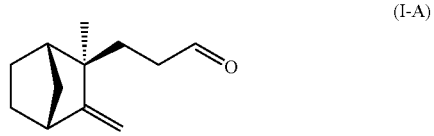

(I-A)

wherein the bold and hatched line indicate an absolute configuration, said compound (I-A) preferably having an e.e. of at least 80%, 90% or above 95%;

from 1 to 8% w/w of 3-((1S,2S,4R)-2-methyl-3-methylenebicyclo[2.2.1]heptan-2-yl)propanal, of formula

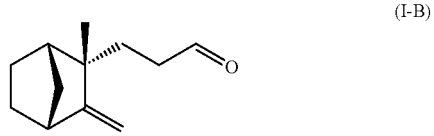

(I-B)

wherein the bold and hatched line indicate an absolute configuration, said compound (I-B) preferably having are e.e. of at least 80%, 90% or above 95%;

from 40 to 60% w/w of 3-((1S,3R,4S)-2,3-dimethyltricyclo[2.2.1.0$^{2,6}$]heptan-3-yl)propanal, of formula

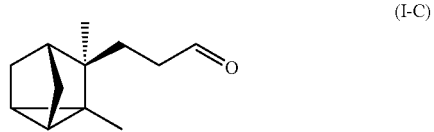

(I-C)

wherein the bold and hatched line indicate an absolute configuration, said compound (I-C) preferably having an e.e. of at least 80%, 90% or above 95%; and from 5 to 20% w/w of 3-((1S,5S,6R)-2,6-dimethylbicyclo[3.1.1]hept-2-en-6-yl)propanal, of formula

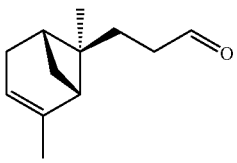

(I-D)

wherein the bold and hatched line indicate an absolute configuration, said compound (I-D) preferably having an e.e. of at least 80%, 90% or above 95%;
the w/w ratio being relative to the total weight of the oxidized terpenes fraction (I).

For the sake of clarity it is well understood to a person skilled in the art that the sum of the amount of the compounds (I-A) to (I-D) is at maximum 100% and at minimum 65% (as obtained by the minimal amount described) and that if the total sum is below 100% the remaining amount can be constituted by other compounds, preferably derived from the oxidation of other natural sesquiterpene hydrocarbons, such as farnesenes, curcumene, bisabolenes, α-pinene, camphene and/or limonene (e.g. see below text regarding the origin of the starting material used in the preparation of such oxidized terpenes fraction). According to a particular embodiment the compounds (I-A) to (I-D) do account for at least 80%, 85%, 90%, 95% w/w relative to the total weigh of the oxidized terpenes fraction.

For the sake of clarity it is well understood by a person skilled in the art that the expression "e.e." has the meaning of the art, i.e. "enantiomeric excess".

Further object of the present invention includes an original method to produce said oxidized terpenes fraction via oxidation of sesquiterpene hydrocarbons fraction, preferably produced by fermentation using santalenes terpene synthases, as well as the use of said oxidized terpenes fraction to produce sandalwood oil building blocks.

In view of the above, it can be easily be seen that compound (I-A) is a precursor of (−)-(Z)-β-santalol, (I-B) is a precursor of (−)-(Z)-epi-β-santalol, (I-C) is a precursor of (+)-(Z)-α-santalol and (I-D) is a precursor of (Z)-α-trans-bergamotol. Therefore the present method presents the advantage of providing an oil comprising already at once all the main constituents of the natural oil, to the contrary of all the prior art methods and intermediate which could allow to produce only one or maximum 2 of said constituent at once.

According to a particular embodiment of the invention, said oxidized terpenes fraction (I) comprises:
from 20 to 35% w/w of the compound of formula (I-A);
from 1 to 5% w/w of the compound of formula (I-B);
from 40 to 55% w/w of the compound of formula (I-C); and
from 10 to 20% w/w of the compound of formula (I-D).

According to any one of the above embodiments of the invention, said oxidized terpenes fraction (I) is characterized by a w/w % ratio (I-C)/(I-D) comprised between 4/1 and 2/1 (e.g between 50%/13% and 30%/15%).

According to any one of the above embodiments of the invention, said oxidized terpenes fraction (I) is characterized by a w/w % ratio (I-C)/(I-A) comprised between 3/1 and 1/1 (e.g between 60%/20% and 30%/30%).

Said oxidized terpenes fraction (I) can be advantageously prepared by a process comprising the following step of reacting a sesquiterpene hydrocarbons fraction (II) comprising
i) from 10 to 30% w/w of (1S,2R,4R)-2-methyl-3-methylene-2-(4-methylpent-3-en-1-yl)bicyclo[2.2.1]heptane (also known as (−)-β-santalene), of formula

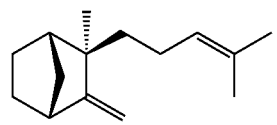

(II-A)

wherein the bold and hatched line indicate an absolute configuration, said compound (II-A) preferably having an e.e. of at least 80%, 90% or 95%;
ii) from 1 to 6% w/w of (1S,2S,4R)-2-methyl-3-methylene-2-(4-methylpent-3-en-1-yl)bicyclo[2.2.1]heptane (also known as (+)-epi-β-santalene), of formula

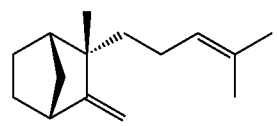

(II-B)

wherein the bold and hatched line indicate an absolute configuration, said compound (II-B) preferably having an e.e. of at least 80%, 90% or 95%;
iii) from 20 to 50% w/w of (2S,4S,7R)-1,7-dimethyl-7-(4-methylpent-3-en-1-yl)tricyclo[2.2.1.0$^{2,6}$]heptane (also known as (+)-α-santalene), of formula

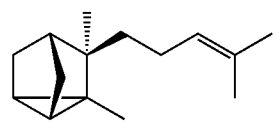

(II-C)

wherein the bold and hatched line indicate an absolute configuration, as said compound (II-C) preferably having an e.e. of at least 80%, 90% or 95%; and
iv) from 20 to 40% w/w (1S,5S,6R)-2,6-dimethyl-6-(4-methylpent-3-en-1-yl)bicyclo[3.1.1]hept-2-ene (also known as (−)-α-trans-bergamotene), of formula

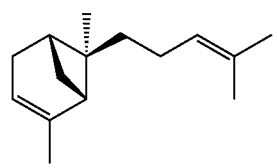

(II-D)

wherein the bold and hatched line indicate an absolute configuration, as said compound (II-D) preferably having an e.e. of at least 80%, 90% or 95%;
the w/w ratio being relative to the total weight of the sesquiterpene hydrocarbons fraction (II);
with ozone under reductive conditions.

According to any one of the above embodiments of the invention, said sesquiterpene hydrocarbons fraction (II) comprises:

from 15 to 30% w/w of the compound of formula (II-A);
from 1 to 6% w/w of the compound of formula (II-B);
from 20 to 40% w/w of the compound of formula (II-C); and
from 20 to 40% w/w of the compound of formula (II-D).

According to any one of the above embodiments of the invention, said sesquiterpene hydrocarbons traction (II) is characterized by a w/w % ratio (II-C)/(II-D) comprised between 2/1 and 1/2 (e.g between 40%/20% and 20%/40%).

According to any one of the above embodiments of the invention, said sesquiterpene hydrocarbons fraction (II) is characterized by a w/w % ratio (II-C)/(II-A) comprised between 3/1 and 1/1 (e.g between 60%/20% and 30%/30%).

For the sake of clarity, it is well understood by a person skilled in the art that the sum of the amount of the compounds (II-A) to (II-D) is at maximum 100% and at minimum the 65% (as obtained by the minimal amount described) and that if the total sum is below 100% the remaining amount can be constituted by other terpene compounds, such as farnesenes, curcumene, bisabolenes, α-pinene, camphene and/or limonene (e.g. see below text regarding the origin of the sesquiterpene hydrocarbons fraction). According to a particular embodiment the compounds (II-A) to (II-D) do account for at least 80%, 85%, 90%, 95% w/w relative to the total weigh of the sesquiterpene hydrocarbons fraction (II).

As mentioned above, the substrate (II) is reacted with ozone, an oxidizing agent. For the sake of clarity, by the expression "under reductive conditions" it is understood by a person skilled in the art that the intermediate trioxolane formed, to obtain aldehydes, is treated with at least one reducing agent, which is well known to a person skilled in the art. Such treatment with a reducing agent can be performed during the work-up. As non limiting examples of said reducing agents one may cite the following: a sulfite, such as an alkaline sulfite (e.g. sodium or potassium sulfite, sodium bisulfite) or a $C_{2-6}$ dialkyl sulfide such as dimethyl sulfide, triphenylphosphine, $H_2$, and Pd/C, $P(OMe)_3$, MeO(SO)OMe, MeSSMe, etc. In particular one may cite a sulfite, such as an alkaline sulfite (e.g. sodium or potassium sulfite, sodium bisulfite) or a $C_{2-6}$ dialkyl sulfide such as dimethyl sulfide.

The oxidation process can be carried out in the presence or absence of a solvent. When a solvent is required or used for practical reasons, then any solvent wherein the sesquiterpene hydrocarbons fraction is soluble and which is of current use in oxidation or ozonolysis reactions can be used for the purposes of the invention. Non-limiting examples include $C_{6-10}$ saturated hydrocarbon solvents such as hexane or cyclohexane, saturated $C_{4-10}$ ethers or esters such as AcOEt, tetrahydroluran, dioxane or MTBE, saturated $C_{2-5}$ carboxylic acids such as acidic or propionic acid, saturated $C_{1-5}$ polar solvents such as primary or secondary alcohols such as isopropanol, methanol or ethanol, saturated $C_{2-6}$ ketones such as butanone or isobuthylmethylketone, $C_{1-3}$ chlorinated alkane such as chloroform or dichloromethane, or mixtures thereof. The exact choice of the solvent is a function of the nature of the exact sesquiterpene hydrocarbons fraction and reaction speed required and the person skilled in the art is well able to select the solvent most convenient in each case to optimize the oxidation reaction.

The solvent can be added to the reaction medium in a large range of concentrations. As non-limiting examples, one can cite as solvent amounts ranging from 50% to 500% w/w, relative to the amount sesquiterpene hydrocarbons fraction used.

The temperature at which the oxidation can be carried out is comprised between −100° C., and 40° C. more preferably in the range of between −80° C., and 0° C. Of course, a person skilled in the art is also able to select the preferred temperature as a function of the melting and boiling point of the starting and final products as well as the desired time of reaction or conversion.

The oxidizing agent, an essential parameter of the process, can be added to the reaction medium in a large range of concentrations. As non-limiting examples, one can cite as oxidizing agent concentration values ranging from 0.2 molar equivalents to 1.5 molar equivalents, relative to the amount sesquiterpene hydrocarbons fraction (II). Preferably, the oxidizing agent concentration will be comprised between 0.5 molar equivalents to 1.2 molar equivalents. It goes without saying that the optimum concentration of oxidizing agent will depend, as the person skilled in the art knows, on the nature of the latter, on the nature of the exact composition of sesquiterpene hydrocarbons fraction, the desired conversion, as well as the desired time of reaction.

The reducing agent, an essential parameter of the process, can be added to the reaction medium in a large range of concentrations. As non-limiting examples, one can cite as reducing agent concentration values those ranging from 0.2 molar equivalents to 3 molar equivalents, relative to the amount sesquiterpene hydrocarbons fraction (II). Preferably, the reducing agent concentration will be comprised between 0.9 molar equivalents to 2.5 molar equivalents. It goes without saying that the optimum concentration of reducing agent will depend, as the person skilled in the art knows, on the nature of the latter, on the nature of the exact composition of sesquiterpene hydrocarbons fraction, the desired conversion, as well as the desired time of reaction.

The sesquiterpene hydrocarbons fraction (II) can be obtained either by admixing the pure sesquiterpene hydrocarbons together in the desired amount, or more interestingly it can obtained as a sesquiterpene hydrocarbons fraction produced by fermentation using host cells, such as microbial cells, genetically engineered to convert unexpensive carbon sources (such as sugar) into the desired sesquiterpene hydrocarbons fraction by using a (+)-α-santalene/(−)-β-santalene synthase as described in WO 2011/000026 or in WO 2010/067309. The advantage of using a sesquiterpene hydrocarbons fraction (II) obtained by fermentation is evident since it allows an easy access to the starting material.

According to any one of the above embodiments of the invention's process, said process is further characterized in that the sesquiterpene hydrocarbons fraction (II) is obtained in a previous step wherein a terpene synthase (as known from the prior art) is contacted with farnesyl-diphosphate (FPP) to produce said sesquiterpene hydrocarbons fraction (II).

The invention's oxidation process, quite surprisingly, provides the following advantages;
  excellent yields on compounds (I-A) to (I-C), while preserving the initial w/w ratio between said (I-A) to (I-C),
  it allows decreasing only the amount of compound (I-D) present in the final product in respect to the amount of (II-D) present in the sesquiterpene hydrocarbons fraction, thus modulating the (Z)-α-trans-bergamotol present in the final sandalwood oil building block.

These are important advantages since, in the production of sesquiterpene hydrocarbons fraction using santalene synthases recombinantly expressed in microorganisms, the prior art data shows that (−)-α-trans-bergamotene is generally produced in quantities exceeding the amounts of (Z)-α-trans-bergamotol generally found in the natural sandalwood oil, which is obviously not suitable. Therefore the current process allows to achieve greater flexibilities in the specification of the sesquiterpene hydrocarbons fraction production.

Moreover, as previously mentioned, the yields provided on (I-A) to (I-C) are excellent, despite that (I-A) and (I-B) do have other double bonds which can be oxidized and thus decrease the yield.

A further aspect of the present invention concerns the use of the oxidized terpenes fraction (I) as starting material for preparing sandalwood oil building block. Indeed the main products present in natural sandalwood oil are (+)-(Z)-α-santalol ((2S,4S,7R)-(Z)-5-(2,3-Dimethyltricyclo[2.2.1.0$^{2,6}$]hept-3-yl)-2-methylpent-2-en-1-ol), (−)-(Z)-β-santalol ((1S,2R,4R)-(2Z)-2-Methyl-5-[2-methyl-3-methylene-bicyclo[2.2.1]hept-2-yl]pent-2-en-1-ol), (−)-(Z)-epi-β-santalol ((1S,2S,4R)-(2Z)-2-Methyl-5-[2-methyl-3-methylene-bicyclo[2.2.1]hept-2-yl]pent-2-en-1-ol), (Z)-α-trans-bergamotol ((2S,4S,7R)-(Z)-5-(2,6-dimethylbicyclo[3.1.1]hept-2-en6-yl)-2-methylpent-2-en-1-ol), so all products which can directly be obtained by the constituents of the oxidized terpenes fraction (I).

For the sake of clarity, by "sandalwood oil building block" it is meant a composition of matter comprising:
a) from 20 to 35% w/w, preferably from 20 to 30% w/w, of (−)-(Z)-β-santalol
b) from 1 to 8% w/w, preferably from 2 to 6% w/w, of (−)-(Z)-epi-β-santalol
c) from 40 to 80% w/w, preferably from 45 to 65% w/w, of (+)-(Z)-α-santalol, and
d) from 3 to 25% w/w, preferably from 5 to 20% w/w, of (Z)-α-trans-bergamotol
the w/w ratio being relative to the total weight of the sandalwood oil building block.

According to any one of the above embodiments of the invention's process, said sandalwood oil building block is characterized by
a w/w % ratio (+)-(Z)-α-santalol/(Z)-α-trans-bergamotol comprised between 10/1 and 3/1, or even 5/1, (e.g between 60%/6% and 50%/10%); and/or
a w/w % ratio (+)-(Z)-α-santalol/(−)-(Z)-β-santalol comprised between 3/1 and 3/2 (e.g between 60%/30% and 30%/20%).

For the sake of clarity it is well understood by a person skilled in the art that the sum of the amount of the constituents a) to d) is at maximum 100% and at minimum the 64% (as obtained by the minimal amount described) and that if the total sum is below 100% the remaining amount can be constituted by other compounds, preferably derived from other natural terpenes. The variance in the amount of said various constituents a) to d) is due to the variance observed in the natural oil, which depends on the botanical species used to produce the oil and the growing conditions (e.g. the weather).

Such composition of matter is considered as a building block since can be used, according to the general knowledge of perfumery, to formulate sandalwood oil reconstitution, e.g. by adding additional perfumery ingredients. It is however also understood that said building blocks can also be used as such to impart odor note of the sandalwood type.

The conversion of said oxidized terpenes fraction (I) into sandalwood oil building blocks can be done using any suitable method known in the art, as for example the ones described in EP 10213 and/or WO 08/120175.

For the sake of clarity in the fore coining, it will be further referred to the oxidized terpenes fraction (I) also by "composition of matter of formula R—CH$_2$CHO", wherein R represents groups of formula:

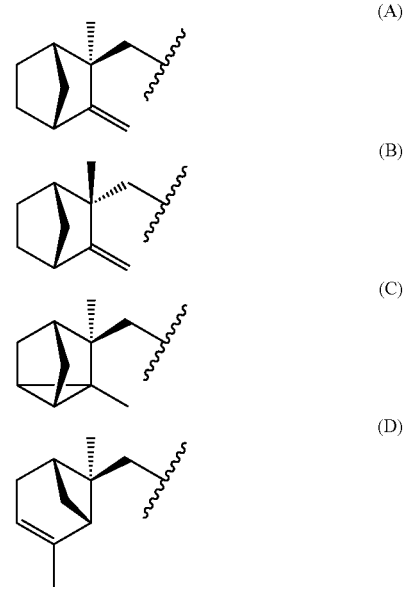

and the wording "composition of matter" indicates we refer to a composition of the four possible compounds in w/w ratio as indicated above for said oxidized terpenes fraction (I). Similarly when it is further referred to a "composition of matter of formula R—", it is meant again a composition of matter of four possible compounds, and in w/w ratio, as defined for R—CH$_2$CHO, the only difference would be in the CH$_2$CHO group which may be transformed into another one.

A non limiting example, typically, the oxidized terpenes fraction (I) can be converted into a sandalwood oil building block, by performing the following reactions:
a) coupling an oxidized terpenes fraction (I) of formula R—CH$_2$CHO, with propionaldehyde (Aldol condensation) to obtain a composition of matter of aldehyde R—CH$_2$CH=CMeCHO (III);
b) converting said composition of matter of aldehyde R—CH$_2$CH=CMeCHO, (III) into the corresponding composition of matter of dienol R—CH=CH—CMe=CHOR$^1$ (IV), wherein R$^1$ represents a C$_1$-C$_3$ alkyl, alkenyl or acyl group or a C$_3$-C$_8$ silyl group;
c) reducing composition of matter of dieneol R—CH=CH—CMe=CHOR$^1$ (IV) into composition of matter of precursor R—CH$_2$CH=CMe-CH$_2$OR$^1$ (V), wherein R$^1$ is as defined in formula (V), and said moiety CH$_2$CH=CMe-CH$_2$OR$^1$ (V) is in the form of any one of its stereoisomers or mixture thereof; and
d) transforming said composition of matter of precursor R—CH$_2$CH=CMe-CH$_2$OR$^1$ (V) into a composition of matter of precursor R—CH$_2$CH=CMe-CH$_2$OH (VI) (the sandalwood oil building block), and said moiety CH$_2$CH=CMe-CH$_2$OH is in the form of any one of its stereoisomers or mixture thereof.

For the sake of clarity, by the expression "said moiety . . . is in the form of any one of its stereoisomers or mixture thereof" for the composition (V) or (VI), in the present context means that the carbon-carbon double bond is in the form of a E or Z isomer or of a mixture thereof. According to any one of the above embodiments of the invention, said compounds (I) are those which are in the form of mixture of E and Z isomers and the Z isomer account for at least 85% w/w of said mixture, or even at least 95%, or even at least 98%.

The above process is also described in Scheme 1.

Scheme 1: Conversion of the oxidized terpenes fraction (I) into the sandalwood oil building block

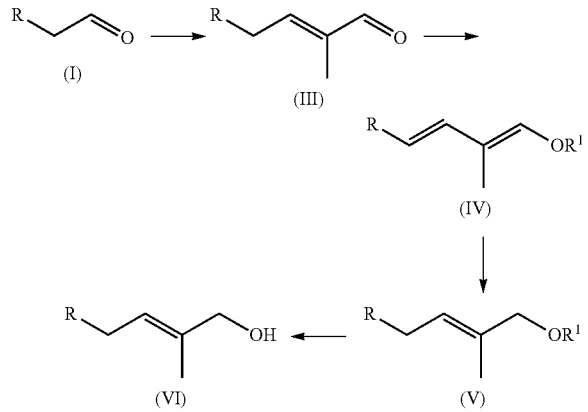

Steps a) to e) can be performed according to standard methods well-known by a person skilled in the art.

For instance, one may cite the following method for each step:

step a) according to EP 10213;
step b) according to Simmons et al. in Helv. Chim. Acta, 1988, 71, 1000;
step c) according to Shibasaki et al., in J. Org. Chem., 1988, 53, 1227 (where is reported the [1,4] hydrogenation of a dienol acetate derivative) or according to WO 08/120175; and
step d) is a simple ester hydrolysis which is well known to a person skilled in the art.

An example of such procedure is provided in the Examples herein below.

EXAMPLES

The invention, in all its embodiments, will now be described in further detail by way of the following examples, wherein the abbreviations have the usual meaning, in the art, the temperatures are indicated in degrees centigrade (° C.); the NMR spectral data were recorded in CDCl$_3$ with a 400 MHz or 125 MHz machine for $^1$H or $^{13}$C respectively, the chemical shifts δ are indicated in ppm with respect to TMS as standard, the coupling constants J are expressed in Hz.

A sesquiterpene hydrocarbons fraction (II) comprising:
about 19.5% w/w of the compound of formula (II-A);
about 2.5% w/w of the compound of formula (II-B);
about 33.4% w/w of the compound of formula (II-C)
about 38.4% w/w of the compound of formula (II-D); and
about 5% w/w of β-(Z)-farnesene
(w/w % being relative to the total weight of the sesquiterpene hydrocarbons fraction (II)) was obtained using *E. coli* cells engineered to overproduced farnesyl diphosphate (FPP) from an heterologous mevalonate pathway and co-expressing a plant-derived terpene synthase. The genetic engineering and use of the *E. coli* host cells has been previously described in WO 2013064411 or in *J. Am. Chem. Soc.* 2012, 134:18900-18903. Briefly, an expression plasmid was constructed containing two operons composed of the genes encoding the enzymes for a complete mevalonate biosynthetic pathway. A first synthetic operon consisting of an *E. coli* acetoacetyl-CoA thiolase (atoB), a *Staphylococcus aureus* HMG-CoA synthase (mvaS), a *Staphylococcus aureus* HMG-CoA reductase (mvaA) and a *Saccharomyces cerevisiae* FPP synthase (ERG20) genes was synthesized in-vitro (DNA2.0, Menlo Park, Calif., USA) and cloned into the pACYCDuet-1 vector (Invitrogen) yielding pACYC-29258. A second operon containing a mevalonate kinase (MvaK1), a phosphomevalonate kinase (MvaK2), a mevalonate diphosphate decarboxylase (MvaD), and an isopentenyl diphosphate isomerase (idi) was amplified from genomic DNA of *Streptococcus pneumoniae* (ATCC BAA-334) and subcloned into the second multicloning site of pACYC-29258 providing the plasmid pACYC-29258-4506. This plasmid thus contains the genes encoding all the enzymes of the biosynthetic pathway leading from acetyl-CoA to FPP. *E. coli* cells (BL21 Star™(DE3), Invitrogen) were co-transformed with the plasmids pACYC-29258-4506 and a pETDuet-1 (Invitrogen) derivative: pETDuet-SCH10-Tps8201-opt containing a codon-optimized version (for expression in *E. coli*) of a cDNA encoding for a *Santalum album* (+)-α-santalene/(−)-β-santalene synthase (Example 6 in WO2010067309). The resulting recombinant cells were used to produce the desired terpene fraction by using fed-batch, high cell density cultivations in laboratory-scale bioreactors essentially as described (*J. Am. Chem. Soc.* 2012, 134:18900-18903). The sesquiterpene fraction was purified from the fermentation broth using a downstream process based on a liquid/liquid extraction and a fractional distillation. This process yields a >90% pure sesquiterpene fraction.

Example 1

Preparation of Oxidized Terpenes Fraction (I)—Oxonolysis

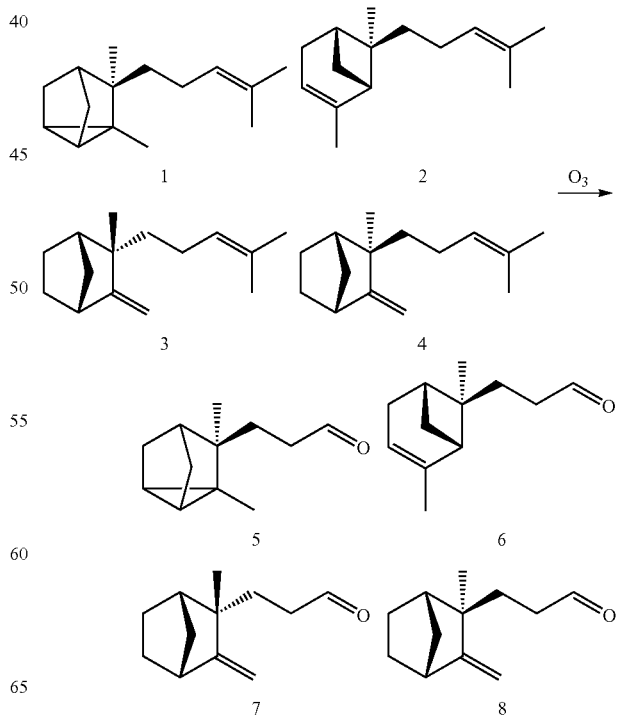

In a 500 ml ozonation flask, a solution of 19.6 g (95 mmol) of sesquiterpene hydrocarbons fraction (II) above described in dichloromethane (200 mL) was cooled at −78° C. Ozone (5.47 g, 1.2 eq) was sparked through the solution at −78° C. Then, solution was purged with oxygen during 10 minutes and after with nitrogen during 15 minutes. Mixture was allowed to return at 0° C. and a solution of sodium sulfite (24 g, 20 eq) in water (250 mL) previously cooled at 0° C. was added. Mixture was stirred 10 minutes at 0° C. and 30 minutes at room temperature. After decantation, layers were separated and aqueous layer was extracted with Et$_2$O. Organic layers were washed with water and then brine. The combined organic layers were dried over MgSO$_4$ and filtered. Solvents were removed under vacuum and the residue (yellow oil) was purified by flash chromatography (Eluant cyclohexane/AcOEt) to afford 8.9 g (53% overall yield) of oxidized terpenes fraction (I) comprising the compounds (I-A)/(I-B)/(I-C)/(I-D) in the w/w % of 26/3/49/15 respectively.

Yield of compound (I-A), calculated on (II-A): 71%
Yield of compound (I-C), calculated on (II-C): 75%
Yield of compound (I-D), calculated on (II-D): 21%

Example 2

Preparation of a Sandalwood Oil Building Block

The oxidized terpenes fraction (I) obtained in example 1 was converted according to Scheme 1 and WO 08/120175.

Aldol step a): propanal 3 molar equivalents, Hexahydroazepinium benzoate 1.0M in water 0.4 eq, toluene, 110° C., 4 hours; Yield=74%

Dieneol ester step b): Ac$_2$O 3 molar equivalents, Et$_3$N 1 molar equivalent, AcOK 0.22 molar equivalent, 120° C., 4 hours; Yield=84%

Reduction of dieneol step c): Maleic acid 0.16 molar equivalents, RuCp*(COD)BF$_4$ 0.01 molar equivalents, acetone, H$_2$, 4 bars, 60° C., 4 hours Hydrolysis of step d): K$_2$CO$_3$ 1.2 molar equivalents, MeOH, 1 hour at room temperature Yield=68% over step d) and c)

In the final sandalwood oil building block obtained the ratio of the various sesquiterpene allylic alcohols corresponds to the same ratio of the corresponding compounds in the oxidised terpenes fraction (I) obtained in example 1.

The invention claimed is:

1. A composition of matter consisting in an oxidized terpenes fraction (I) comprising:

from 15 to 40% w/w of 3-((1S,2R,4R)-2-methyl-3-methylenebicyclo[2.2.1]heptan-2-yl)propanal, of formula

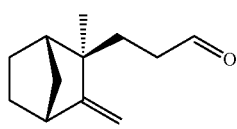

(I-A)

wherein the bold and hatched line indicate an absolute configuration;

from 1 to 8% w/w of 3-((1S,2S,4R)-2-methyl-3-methylenebicyclo[2.2.1]heptan-2-yl)propanal, of formula

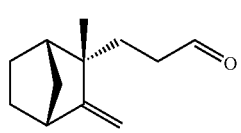

(I-B)

wherein the bold and hatched line indicate an absolute configuration;

from 40 to 60% w/w of 3-((1S,3R,4S)-2,3-dimethyltricyclo[2.2.1.0$^{2,6}$]heptan-3-yl)propanal, of formula

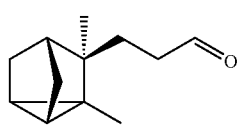

(I-C)

wherein the bold and hatched line indicate an absolute configuration; and from 5 to 20% w/w of 3-((1S,5S,6R)-2,6-dimethylbicyclo[3.1.1]hept-2-en-6-yl)propanal, of formula

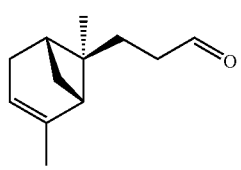

(I-D)

wherein the bold and hatched line indicate an absolute configuration;

the w/w ratio being relative to the total weight of the oxidized terpenes fraction (I).

2. The composition of claim 1, wherein said composition comprises:

from 20 to 35% w/w of the compound of formula (I-A);
from 1 to 5% w/w of the compound of formula (I-B);
from 40 to 55% w/w of the compound of formula (I-C); and
from 10 to 20% w/w of the compound of formula (I-D).

3. The composition of claim 1, wherein said composition comprises:

a w/w % ratio (I-C)/(I-D) comprised between 4/1 and 2/1; and/or
a w/w % ratio (I-C)/(I-A) comprised between 3/1 and 1/1.

4. The composition of claim 1, wherein said compounds (I-A), (I-B), (I-C) and (I-D) have an e.e. of at least 80%.

5. A process for the preparation of a composition of matter, as defined in claim 1, comprising reacting:

a sesquiterpene hydrocarbons fraction (II) comprising
i) from 10 to 30% w/w of (1S,2R,4R)-2-methyl-3-methylene-2-(4-methylpent-3-en-1-yl)bicyclo[2.2.1]heptane (also known as (−)-β-santalene), of formula

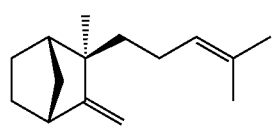

(II-A)

wherein the bold and hatched line indicate an absolute configuration;

ii) from 1 to 6% w/w of (1S,2S,4R)-2-methyl-3-methylene-2-(4-methylpent-3-en-1-yl)bicyclo[2.2.1]heptane (also known as (+)-epi-β-santalene), of formula

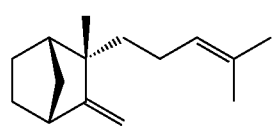

(II-B)

wherein the bold and hatched line indicate an absolute configuration;

iii) from 20 to 50% w/w of (2S,4S,7R)-1,7-dimethyl-7-(4-methylpent-3-en-1-yl)tricyclo[2.2.1.0²,⁶]heptane (also known as (+)-α-santalene), of formula

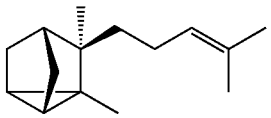

(II-C)

wherein the bold and hatched line indicate an absolute configuration; and iv) from 20 to 40% w/w of (1S,5S,6R)-2,6-dimethyl-6-(4-methylpent-3-en-1-yl)bicyclo[3.1.1]hept-2-ene (also known as (−)-α-trans-bergamotene), of formula

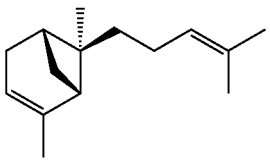

(II-D)

wherein the bold and hatched line indicate an absolute configuration;
the w/w ratio being relative to the total weight of the sesquiterpene hydrocarbons fraction (II)
with ozone under reductive conditions.

6. The process of claim 5, wherein said sesquiterpene hydrocarbons fraction (II) comprises:
  a w/w % ratio (II-C)/(II-D) comprised between 2/1 and 1/2; and/or
  a w/w % ratio (II-C)/(II-A) comprised between 3/1 and 1/1.

7. The process according to claim 5, wherein said reductive conditions are performed with an alkaline sulfite or a $C_{2-6}$ dialkyl sulfide.

8. The process of claim 5, wherein said sesquiterpene hydrocarbons fraction (II) is obtained in a previous step wherein a terpene synthase is contacted with farnesyl-diphosphate (FPP) to produce said sesquiterpene hydrocarbons fraction (II).

9. A method for preparing a sandalwood oil building block comprising utilizing the oxidized terpenes fraction (I) of claim 1 as a starting material for preparing a sandalwood oil building block.

10. The method of claim 9, wherein the sandalwood oil building block is a composition of matter comprising:
  a) from 20 to 35% w/w, of (−)-(Z)-β-santalol;
  b) from 1 to 8% w/w, of (−)-(Z)-epi-β-santalol;
  c) from 40 to 80% w/w, of (+)-(Z)-α-santalol; and
  d) from 3 to 25% w/w, of (Z)-α-trans-bergamotol.

11. The method of claim 9, wherein the sandalwood oil building block is a composition of matter comprising:
  a) from 20 to 30% w/w, of (−)-(Z)-β-santalol;
  b) from 2 to 6% w/w, of (−)-(Z)-epi-β-santalol;
  c) from 45 to 65% w/w, of (+)-(Z)-α-santalol; and
  d) from 5 to 20% w/w, of (Z)-α-trans-bergamot

* * * * *

UNITED STATES PATENT AND TRADEMARK OFFICE
CERTIFICATE OF CORRECTION

PATENT NO. : 9,879,203 B2
APPLICATION NO. : 15/529300
DATED : January 30, 2018
INVENTOR(S) : Knopff et al.

Page 1 of 1

It is certified that error appears in the above-identified patent and that said Letters Patent is hereby corrected as shown below:

On the Title Page

Item (87) PCT Pub. Date, delete "Jun. 9, 2010" and insert -- Jun. 9, 2016 --.

In the Claims

Column 14:
Line 30, Claim 11, delete "(Z)-α-trans-bergamot" and insert -- (Z)-α-trans-bergamotol --.

Signed and Sealed this
Tenth Day of July, 2018

Andrei Iancu
*Director of the United States Patent and Trademark Office*